United States Patent [19]
Brenner et al.

[11] 3,985,896
[45] Oct. 12, 1976

[54] BENZOPHENALENOFURANS

[75] Inventors: L. Martin Brenner, Havertown; Charles K. Brush, Malvern, both of Pa.

[73] Assignee: SmithKline Corporation, Philadelphia, Pa.

[22] Filed: July 15, 1975

[21] Appl. No.: 596,114

[52] U.S. Cl............................. 424/285; 424/267; 424/248; 424/274; 424/250; 260/293.58; 260/326.5 C; 260/268 PC; 260/346.2 M; 260/346.2 R; 260/256; 260/247.7 T

[51] Int. Cl.$^2$................. C07D 307/80; A61K 31/34

[58] Field of Search ............ 260/346.2 M, 326.5 C, 260/293.58; 424/285, 267, 274

[56] References Cited
OTHER PUBLICATIONS

Schönberg et al., Chem. Ber., vol. 105, pp. 1562–1567, (1972).

*Primary Examiner*—Natalie Trousof
*Assistant Examiner*—Bernard Dentz
*Attorney, Agent, or Firm*—Janice E. Williams; Joan S. Keps; William H. Edgerton

[57] ABSTRACT

The compounds are benzophenalenofurans having pharmacological activity, in particular, coronary vasodilator activity.

6 Claims, No Drawings

BENZOPHENALENOFURANS

This invention relates to new benzophenalenofurans which have useful pharmacological activity. More specifically, these compounds have coronary vasodilator activity.

The benzophenaloenofurans of this invention are represented by the following structural formula:

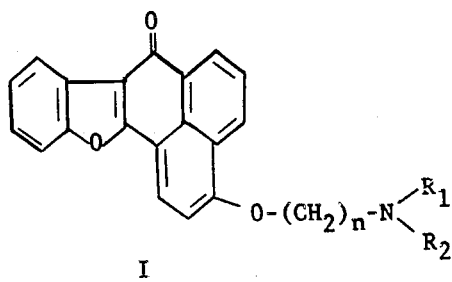

I or a pharmaceutically acceptable acid addition salt thereof, in which:
  $R_1$ is hydrogen or lower alkyl and
  $R_2$ is lower alkyl or
  $R_1$ and $R_2$ together with the nitrogen atom to which they are attached form a pyrrolidine, piperidine, N-(lower alkyl)piperazine, morpholine or perhydroazepine ring; and
  $n$ is 2 or 3.

As used herein the term "lower alkyl" denotes groups having from one to four carbon atoms.

Advantageous compounds of this invention are represented by formula I in which $R_1$ is hydrogen or lower alkyl and $R_2$ is lower alkyl.

Preferred compounds of this invention are represented by formula I in which $R_1$ is hydrogen or lower alkyl, $R_2$ is lower alkyl and $n$ is 2.

Particularly preferred is the compound 3-(2-diethylaminoethoxy)-7-oxo-7H-benzo[b]phenaleno[2,1-d]furan, which is represented by the following structural formula:

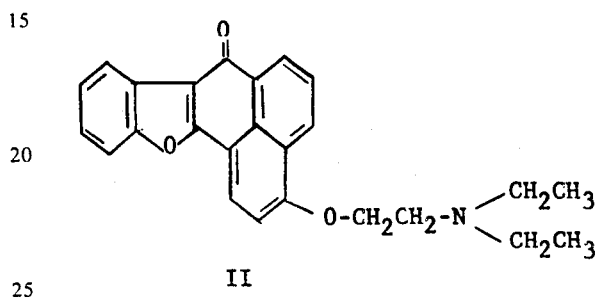

II

The compounds of formula I are preferably, prepared as shown in the following scheme in which the terms $R_1$, $R_2$ and $n$ are defined as above and X is halo, preferably chloro or bromo:

SCHEME 1

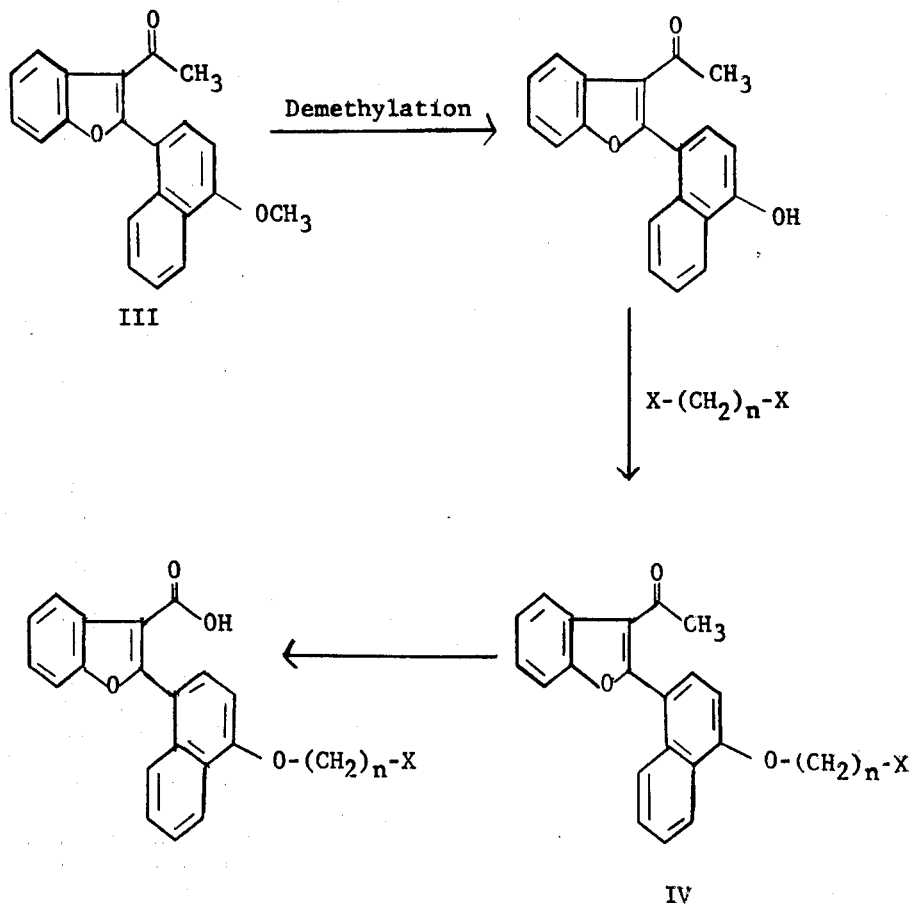

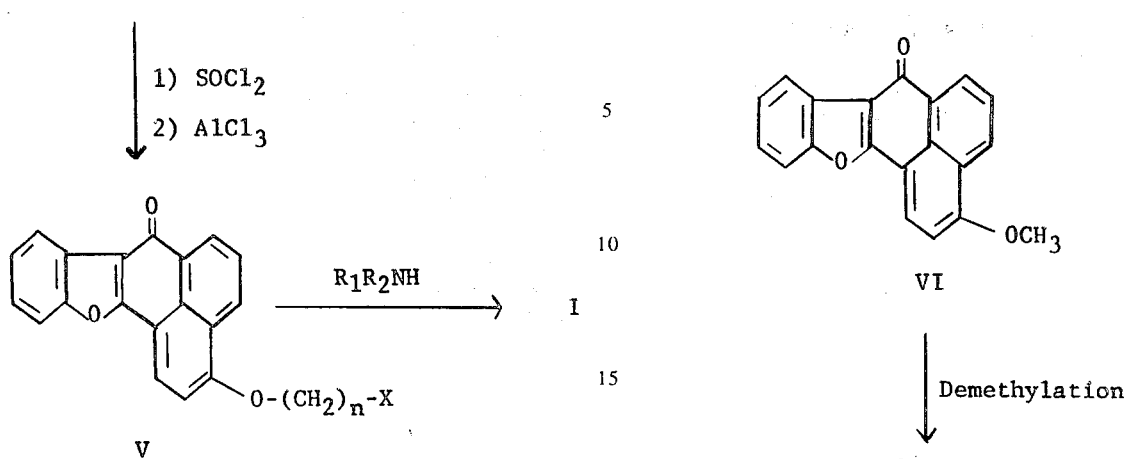

According to Scheme 1, the 3-acetyl-2-(methoxynaphthyl)benzofuran of formula III is demethylated, for example by the use of pyridine hydrochloride or boron tribromide, to give the corresponding hydroxynaphthyl compound. Reaction of the 3-acetyl-2-(hydroxynaphthyl)benzofuran thus formed with a dihaloalkane of the formula X—$(CH_2)_n$—X, preferably dibromo or dichloro, in the presence of a base as potassium carbonate in a solvent such as acetone or 3-pentanone, preferably at the reflux temperature, gives a compound of formula IV. Oxidation of the acetyl function of IV, for example by treatment with sodium hypobromite in aqueous dioxane, with subsequent cyclization of the resulting 3-carboxy-2-(substituted naphthyl)benzofuran, for example by treatment with thionyl chloride followed by reaction with aluminum chloride, gives the benzophenalenofuran derivative V. Treatment of V with an amine of the formula $R_1R_2NH$ where $R_1$ and $R_2$ are defined as above in a solvent such as refluxing ethanol, gives the corresponding compounds of formula I.

The compounds of formula V are, alternatively, prepared from the compounds of formula III as shown in Scheme 2 in which the terms $R_1$, $R_2$ and $n$ are defined as above and X is halo, preferably chloro or bromo:

SCHEME 2

Thus, oxidation of III as previously described followed by cyclization of the product 2-carboxy-3-(methoxynaphthyl)benzofuran also as previously described gives the benzophenalenofuran of formula VI. Demethylation of VI as described above with subsequent treatment of the product thus obtained with the dihaloalkane X—$(CH_2)_n$—X, preferably dichloro or dibromo, as described above gives the corresponding compounds of formula V which are converted to the compounds of formula I as previously described.

The products of formula I are isolated and purified as such by standard techniques including solvent extraction, crystallization and chromatographic methods or as the corresponding acid addition salts which are also objects of this invention. The salts are formed with organic and inorganic acids according to methods known to the art. Thus, a solution of the amine in ether or an alcohol such as methanol or ethanol is treated with a solution of an organic or inorganic acid in an aqueous miscible solvent, such as acetone or ethanol, with isolation of the salt by concentration and cooling or in an aqueous immiscible solvent, such as ether, with the desired salt separating directly. Exemplary of such organic salts are those with maleic, fumaric, benzoic, ascorbic, pamoic, succinic, hexamic, oxalic, bismethylene-salicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is well known to the art. The salts may be purified by the standard methods described above.

The acetyl-methoxynaphthylbenzofuran of formula III is preferably prepared by treatment of the flavyllium salt formed from reaction of ethyl 4-methoxy-1-naphthylketone and salicylaldehyde with hydrogen peroxide as described by Jurd, *J. Org. Chem.* 29:2602 (1964).

The compound of formula III is also prepared by acetylation of 2-(4-methoxynaphthyl)benzofuran by standard methods, for example with acetyl chloride. The 2-(4-methoxynaphthyl)benzofuran starting material is prepared by a variety of methods described in the art such as by coupling of cuprous 4-methoxy-1-naphthylacetylide with o-iodophenol by the method of Castro et al., *J. Org. Chem.* 28:3313 (1963), 31:4071 (1966); *Org. Syn.* Coll. Vol. IV, pg. 327 or by cyclization of 4-methoxy-1-phenoxyacetylnaphthalene with polyphosphoric acid by the method of Chatterjea et al., *J. Indian Chem. Soc.* 47:261 (1970).

The coronary vasodilator activity of the compounds of this invention is demonstrated in dogs by in increase in coronary blood flow with concomitant decrease of mean arterial blood pressure upon intravenous administration of doses of from about 0.63 to about 10.0 mg./kg. These parameters are measured as follows:

Adult mongrel dogs (13–16 kg.) are pretreated with 2 mg./kg. s.c. of morphine sulfate followed in 1 hour by intravenous administration of 1–1.5 ml./kg. of an aqueous solution containing 1.5% chloralose and 20% urethane. Supplemental doses of morphine and chloralose-urethane are given to maintain an adequate and uniform depth of anesthesia.

A carotid artery is catheterized and connected to a Sanborn pressure transducer to measure arterial blood pressure. A femoral vein is also catheterized for administering a solution of the test compound or its salt and supplemental anesthesia. A left thoractomy is made at the fourth or fifth intercostal space, the lung is displaced, the pericardium is opened and the left circumflex coronary artery is isolated for measurement of coronary blood flow, a "snare" being placed around the artery distally to obtain zero flow. Coronary blood flow is measured with a Statham electromagnetic flowmeter and Flo-Probe (MDS).

The pharmacologically active compounds of this invention may be administered orally or parenterally in an amount to produce the desired activity.

Preferably the compounds are administered in conventional dosage unit forms prepared by combining an appropriate dose of the compound with standard pharmaceutical carriers. The dosage units will contain the active ingredient in an amount of from about 100 mg. to about 600 mg., preferably 150 mg. to 300 mg. per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate along or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The pharmaceutical compositions are prepared by conventional techniques involving procedures such as mixing, granulatng and compressing when necessary or variously mixing and dissolving the ingredients as appropriate to the desired composition.

The method of producing coronary vasodilator activity in accordance with this invention comprises administering internally to an animal an effective amount of a compound of this invention. The compound will preferably be administered in a dosage unit form as described above orally or parenterally, the oral route being preferred. Advantageously equal doses will be administered one to two times daily with the daily dosage regimen being from about 200 mg. to about 1200 mg., preferably from about 300 mg. to about 600 mg. When the method described above is carried out, coronary vasodilator activity is produced.

One skilled in the art will recognize that in determining the amounts of the compound needed to produce the desired pharmacological effect without toxic side effects, the activity of the compound as well as the size of the host animal must be considered.

The following examples illustrate the invention but are not to be construed as limiting the scope thereof. Temperatures given herein are in degrees centigrade unless otherwise stated.

When formed, acid addition salts may be converted to the corresponding free amines by treating a solution of the salt in a solvent such as water, a chloroform-water or a benzene-water mixture with a base such as 10% aqueous sodium hydroxide, sodium carbonate or sodium bicarbonate until basic followed by extraction of the amine into benzene or chloroform. Salts other than hydrochlorides may be converted to the corresponding hydrochloric acid salts by passing a solution of the salt in methanol or ethanol through an Amberlite IRA-401 chloride ion exchange column.

PREPARATION 1

3-Acetyl-2-(4-methoxynaphthyl)benzofuran

Method A

Aluminum chloride (43.7 g., 0.317 mol.) was added to a solution of 50.17 g. (0.317 mol.) of 1-methoxynaphthalene in 400 ml. of ethylene dichloride at 0°. The mixture was stirred while a solution of 48.2 g. (0.317 mol.) of phenoxyacetyl chloride in 150 ml. of ethylene dichloride was added dropwise. The reaction mixture was stirred at 0° for 1 hour and for 30 minutes at ambient temperature, then poured into 500 ml. of water and stirred vigorously. The mixture was steam distilled, the residue was cooled and diluted with ether and the solid material was collected by filtration and washed with ether. The layers were separated and the aqueous phase was extracted with ether. The combined ethereal extracts and washings were washed with 10% aqueous sodium bicarbonate solution, dried (MgSO$_4$) and evaporated to give a residue which was combined with the solid material previously isolated and recrystallized from ethanol to give 4-methoxy-1-phenoxyacetylnaphthalene, m.p. 105°–107°.

A solution of 28.4 g. (0.097 mol.) of 4-methoxy-1-phenoxyacetylnaphthalene in polyphosphoric acid, prepared from 274 g. of phosphorus pentoxide and 130 ml. of 85% phosphoric acid, was heated at 170° for 45 minutes. The reaction mixture was cooled, ice water was added and the solution was extracted with ether. The extract was washed with 10% aqueous sodium bicarbonate solution and saturated sodium chloride solution, dried ($MgSO_4$) and evaporated to dryness to give a residue which was chromatographed on Florisil with 1:1 methylene chloride-hexane as eluant to give 2-(4-methoxynaphthyl)-benzofuran.

Acetyl chloride (3.18 ml., 0.045 mol.) was added to a solution of 13.5 g. (0.098 mol.) of aluminum chloride in 100 ml. of nitrobenzene at 0° followed by addition of 12.0 g. (0.044 mol.) of 2-(4-methoxynaphthyl)benzofuran. The reaction mixture was stirred at 0° for 1 hour, then poured into water. The solvent was removed by steam distillation and the residue was dissolved in ether. The ethereal solution was washed with 5% aqueous sodium hydroxide solution and water, dried ($MgSO_4$) and evaporated to dryness to give a residue which was chromatographed on silica with 1:1 methylene chloride-hexane as eluant to give the title compound, m.p. 136°–138°.

Method B

To a suspension of 33.3 g. (0.146 mol.) of 1-(2-carboxyethenyl)-4-methoxynaphthalene in 500 ml. of chloroform was added dropwise a solution of 8.05 ml. (0.146 mol.) of bromine in 125 ml. of methylene chloride. The solvent was removed, a solution of 31 g. (0.292 mol.) of sodium carbonate in 300 ml. of water was added to the residue and the mixture was refluxed for 2 hours. After cooling, the mixture was extracted with methylene chloride, the layers were separated and the organic phase was washed with water and saturated sodium chloride solution, dried ($MgSO_4$) and evaporated to dryness to give 1-(2-bromoethenyl)-4-methoxynaphthalene.

Phenyllithium (164 ml. of 2.1 M, 0.345 mol.) was added dropwise to a solution of 35.9 g. (0.138 mol.) of 1-(2-bromoethenyl)-4methoxynaphthalene in 120 ml. of refluxing dry benzene under a nitrogen atmosphere. After addition the reaction mixture was refluxed for 30 minutes, then ice and water were slowly added. The mixture was shaken, the layers separated and the organic phase was washed with water and saturated sodium chloride solution, dried ($MgSO_4$) and evaporated to give 1-ethynyl-4-methoxynaphthalene.

95% Hydroxylamine hydrochloride (13.9 g., 0.2 mol.) was added to a solution of 25.0 g. (0.1 mol.) of cupric sulfate in 100 ml. of concentrated ammonium hydroxide and 400 ml. of water. The mixture was cooled to 0° and a solution of 15.7 g. (0.086 mol.) of 1-ethynyl-4-methoxy-naphthalene in 400 ml. of ethanol and 100 ml. of tetrahydrofuran was added under a nitrogen atmosphere with vigorous stirring. The precipitate was collected by filtration, washed with copious amounts of water, ethanol and ether, air-dried and dried in vacuo to give 4-methoxy-naphthylacetylide.

A solution of 15.4 g. (0.07 mol.) of o-iodophenol in 200 ml. of pyridine was added under a nitrogen atmosphere to a suspension of 17.0 g. (0.07 mol.) of 4-methoxy-naphthylacetylide in 250 ml. of pyridine. The reaction mixture was heated at 120° for 24 hours, then about 300 ml. of pyridine was removed by distillation in vacuo. The residue was poured into water and the aqueous mixture was extracted with chloroform. The extract was washed with dilute hydrochloric acid, dried ($MgSO_4$) and evaporated to dryness. The residue was chromatographed on Florisil with 1:1 methylene chloride-hexane as eluant to give 2-(4-methoxynaphthyl)-benzofuran.

2-(4-Methoxynaphthyl)benzofuran was acetylated with acetyl chloride as described in Method A above to give the title compound.

Method C

A mixture of 16.7 g. (0.078 mol.) of ethyl 4-methoxynaphthylketone and 9.5 g. (0.078 mol.) of salicylaldehyde in 200 ml. of ethyl acetate and 70 ml. of absolute ethanol was saturated with dry hydrogen chloride gas and allowed to stir for 12 hours at ambient temperature. The reaction mixture was cooled to 0° and the precipitate was collected by filtration and washed with ether to give the corresponding flavyllium chloride salt.

To a solution of 19.45 g. (0.058 mol.) of the flavyllium chloride salt in 500 ml. of methanol was slowly added a solution of 6.8 ml. (0.07 mol.) of 30% hydrogen peroxide in 100 ml. of methanol at ambient temperature. The reaction mixture was stirred for 30 minutes, then poured into 3 l. of water. The aqueous solution was extracted twice with methylene chloride and the combined extracts were dried ($MgSO_4$) and evaporated to dryness. The residue was chromatographed on Florisil with 1:1 methylene chloride-hexane as eluant to give the title compound.

PREPARATION 2

3-(2-Bromoethoxy)-7-oxo-7H-benzo[b]-phenaleno[2,1-d]furan

Method A

A mixture of 13.8 g. (0.044 mol.) of 3-acetyl-2-(4-methoxynaphthyl)benzofuran and 100 g. of pyridine hydrochloride was heated at 185° for 4.5 hours. The hot reaction mixture was poured into an ice-dilute hydrochloric acid mixture and the aqueous solution was extracted with ether. The extract was dried ($MgSO_4$) and evaporated to give 3-acetyl-2-(4-hydroxynaphthyl)benzofuran, m.p. 212°–216°.

To a solution of 11.9 g. (0.039 mol.) of 3-acetyl-2-(4-hydroxynaphthyl)benzofuran in 400 ml. of 2-butanone was added 100 ml. (0.24 mol.) of 1,2-dibromoethane and 22 g. (0.16 mol.) of anhydrous potassium carbonate. The reaction mixture was refluxed for 8 hours, then the solvent was evaporated and the excess 1,2-dibromoethane was removed by distillation in vacuo. The residue was chromatographed on silica with 10% hexane in methylene chloride as eluant to give 3-acetyl-2-[4-(2-bromoethoxy)naphthyl]benzofuran, m.p. 115°–117°.

A solution of sodium hypobromite, prepared by adding 2.45 g. (0.45 mol.) of bromine to a cooled (0°) solution of 4.5 g. (0.1125 mol.) of sodium hydoxide in 40 ml. of water, was added to a solution of 6.1 g. (0.015 mol.) of 3-acetyl-2-[4-(2-bromoethoxy)naphthyl]benzofuran in 60 ml. of dioxane and the mixture was shaken for 12 hours. Sodium bisulfite was added to the reaction mixture, water was added and the mixture was extracted twice with ether. The aqueous phase was acidified with hydrochloric acid, the resulting precipitate was digested on a steam bath for 1 hour, cooled to 0° and collected by filtration to give 3-carboxy-2-[4-(2-bromo-ethoxy)naphthyl]benzofuran, m.p. 260°–265° (dec.).

3-Carboxy-2-[4-(2-bromoethoxy)naphthyl]benzofuran (5.17 g., 12.5 mmol.) and an excess amount of thionyl chloride were refluxed in 100 ml. of methylene chloride for 2 hours. The mixture was evaporated to dryness, cooled to 0° and dry methylene chloride and 2.07 g. (15 mmol.) of anhydrous aluminum chloride were added. The reaction mixture was stirred at 0° for 1 hour then poured into water. The resulting precipitate was collected. The layers were separated and the organic phase was washed with dilute sodium hydroxide solution and saturated sodium chloride solution, dried ($MgSO_4$) and evaporated to dryness. The residue and the precipitate previously collected were combined and recrystallized from toluene to give the title compound, m.p. 206°–209°.

Method B

A solution of sodium hypobromite was prepared by addition of 3.36 g. (0.021 mol.) of bromine to a solution of 2.1 g. (0.0525 mol.) of sodium hydroxide in 30 ml. of water at 0° to which was added a solution of 2.2 g. (0.007 mol.) of 3-acetyl-2-(4-methoxynaphthyl)benzofuran in 50 ml. of dioxane. The reaction mixture was shaken for 12 hours, then a small amount of sodium bisulfite was added and the mixture was extracted with ether. The aqueous phase was acidified with hydrochloric acid and the resulting precipitate digested on a steam bath for 30 minutes, cooled, collected by filtration and recrystallized from ethanol to give 3-carboxy-2-(4-methoxynaphthyl)benzofuran, m.p. 255°–257°.

Thionyl chloride (5 ml.) was added to a suspension of 1.72 g. (54 mmol.) of 3-carboxy-2-(4-methoxynaphthyl)-benzofuran in 75ml. of methylene chloride and the reaction mixture was refluxed for 2.5 hours. The mixture was evaporated to dryness and the residue was dissolved in 100 ml. of methylene chloride to which was added 0.8 g. (0.006 mol.) of anhydous aluminum chloride. The mixture was stirred for 1.5 hours at 0° then at ambient temperature for 30 minutes. The mixture was poured into water, methylene chloride was added to dissolve the precipitate, the layers were separated and the organic phase was washed with aqueous sodium carbonate, dried ($MgSO_4$) and evaporated to dryness. The residue was recrystallized from toluene to give 3-methoxy-7-oxo-7H-benzo[b]phenalene[2,1-d]furan, m.p. 235°–238°.

Alternatively, 3-methoxy-7-oxo-7H-benzo[b]-phenaleno[2,1-d]furan was prepared by addition of 0.38 ml. (45 mmol.) of oxalyl chloride followed by 1.2 ml. (0.01 mol.) of stannic chloride to a solution of 1 g. (37 mmol.) of 2-(4-methoxynaphthyl)benzofuran in 100 ml. of methylene chloride at 0°. The reaction mixture was stirred for 1.5 hours at 0° then poured into water. The layers were separated and the organic phase was washed with 10% aqueous sodium carbonate, dried ($MgSO_4$) and evaporated to dryness. The residue was chromatographed on silica with chloroform as eluant to give the product.

3-Methoxy-7-oxo-7H-benzo[b]phenalene[2,1-d]furan (1 g., 33 mmol.) and 40 g. of pyridine hydrochloride were heated at 185° for 4.5 hours. The mixture was poured into ice-dilute hydrochloric acid and the resulting precipitate was collected by filtration, dried in vacuo and recrystallized from methyl benzoate to give 3-hydroxy-7-oxo-7H-benzo[b]-phenaleno[2,1-d]furan, m.p. 374°.

3-Hydroxy-7-oxo-7H-benzo[b]phenaleno[2,1-d]furan is reacted with 1,2-dibromoethane according to the procedure described in Method A above to give the title compound.

PREPARATION 3

3-(3-Bromopropoxy)-7-oxo-7H-benzo[b]-phenaleno[2,1-d]furan

When an equivalent amount of 1,3-dibromopropane is substituted for 1,2-dibromoethane in the reaction with 3-acetyl-2-(4-hydroxynaphthyl)benzofuran as described in Preparation 2, Method A, 3-acetyl-2-[4-(3-bromopropoxy)naphthyl]benzofuran is prepared.

Treatment of 3-acetyl-2-[4-(3-bromopropoxy)naphthyl]-benzofuran with sodium hypobromite followed by cyclization of the product with aluminum chloride as described above, gives the title compound.

Alternatively, the title compound is prepared by reaction of 3-hydroxy-7-oxo-7H-benzo[b]-phenaleno[2,1-d]furan with 1,3-dibromopropane as previously described.

EXAMPLE 1

3-(2-Diethylaminoethoxy)-7-oxo-7H-benzo[b]-phenaleno[2,1-d]furan

A suspension of 4.4. g. (11.2 mmol.) of 3-(2-bromoethoxy)-7-oxo-7H-benzo[b]phenaleno[2,1-d]furan and 10 ml. of ethylamine in 250 ml. of absolute ethanol was refluxed for 4 days. The reaction mixture was filtered while hot, the filtrate was evaporated to dryness and the semi-solid residue was dissolved in methylene chloride. The methylene chloride solution was extracted twice with dilute sodium hydroxide solution and once with water, dried ($MgSO_4$) and evaporated to dryness to give a residue which was crystallized from hexane to give the title compound, m.p. 115°–118°.

The title compound (3 g.) was dissolved in 500 ml. of boiling acetone. Concentrated hydrochloric acid (2 ml.) was added with vigorous stirring. The solution was cooled and the precipitated 3-(2-diethylaminoethoxy)-7-oxo-7H-benzo[b]phenaleno[2,1-d]furan hydochloride was collected and dried in vacuo, m.p. 246°–249°.

EXAMPLE 2

3-(3-Diethylaminopropoxy)-7-oxo-7H-benzo[b]-phenaleno[2,1-d]-furan

Reaction of 3-(3-bromopropoxy)-7-oxo-7H-benzo[b]-phenaleno[2,1-d]furan with ethylamine as described in the procedure of Example 1 gives the title compound.

The title compound may be converted to the corresponding hydrochloride salt as described in Example 1.

EXAMPLE 3

Substitution of an equivalent amount of a dialkylamine listed below:
 dimethylamine
 dipropylamine
 dibutylamine
in the procedure of Example 1 in place of diethylamine gives the following compounds of this invention:
 3-(2-dimethylaminoethoxy)-7-oxo-7H-benzo[b]-phenaleno[2,1-d]furan
 3-(2-dipropylaminoethoxy)-7-oxo-7H-benzo[b]-phenaleno[2,1-d]furan 3-(2-dibutylaminoethoxy)-7-oxo-7H-benzo[b]-phenaleno[2,1-d]furan.

Likewise, the corresponding 3-(3-dialkylaminopropoxy)benzophenalenofurans are prepared by reaction of an amine listed above with 3-(3-bromopropoxy)-7-oxo-7H-benzo[b]-phenaleno[2,1-d]furan.

EXAMPLE 4

Substitution of an equivalent amount of an alkylamine listed below:
methylamine
ethylamine
propylamine
butylamine
in the procedure of Example 1 in place of diethylamine gives the following compounds of this invention:
3-(2-methylaminoethoxy)-7-oxo-7H-benzo[b]-phenaleno[2,1-d]furan
3-(2-ethylaminoethoxy)-7-oxo-7H-benzo[b]-phenaleno[2,1-d]furan
3-(2-propylaminoethoxy)-7-oxo-7H-benzo[b]-phenaleno[2,1-d]furan
3-(2-butylaminoethoxy)-7-oxo-7H-benzo[b]-phenaleno[2,1-d]furan In a similar manner, the corresponding 3-(3-alkylaminopropoxy)benzophenalenofurans are prepared by reaction of an amine listed above with 3-(3-bromopropoxy)-7-oxo-7H-benzo[b]phenaleno[2,1-d]furan.

EXAMPLE 5

Substitution of an equivalent amount of a heterocyclylamine listed below:
pyrrolidine
piperidine
morpholine
N-methylpiperazine
perhydroazepine
in the procedure of Example 1 in place of diethylamine gives the following compounds of this invention:

3-(2-N-pyrrolidinoethoxy)-7-oxo-7H-benzo[b]-phenaleno[2,1-d]furan
3-(2-N-piperidinoethoxy)-7-oxo-7H-benzo[b]-phenaleno[2,1-d]furan
3-(2-N-morpholinoethoxy)-7-oxo-7H-benzo[b]-phenaleno[2,1-]furan
3-[2-N-(4-methylpiperazino)ethoxy]-7-oxo-7H-benzo[b]phenaleno[2,1-d]furan
3-(2-N-perhydroazepinoethoxy)-7-oxo-7H-benzo[b]-phenaleno[2,1-d]furan.

Likewise, the corresponding 3-(3-heterocyclylamino-propoxy)benzophenalenofurans are prepared by reaction of a heterocyclylamine listed above with 3-(3-bromopropoxy)-7-oxo-7H-benzo[b]-phenaleno[2,1-d]furan.

EXAMPLE 6

Addition of an ethereal solution of oxalic acid to a solution of 3-(2-diethylaminoethoxy)-7-oxo-7H-benzo[b]-phenaleno[2,1-d]furan in ether gives the oxalate salt.

The corresponding hydrochloride salt may be prepared from the oxalate salt by passage of a solution of 3-(2-diethylaminoethoxy)-7-oxo-7H-benzo[b]-phenaleno[2,1-d]furan oxalate in ethanol through an Amberlite IRA-401 chloride ion exchange column.

In a similar manner, other acid addition salts may be prepared.

What is claimed is:
1. A compound of the formula:

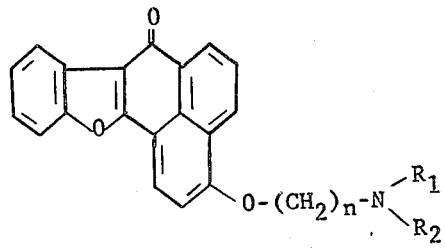

or a pharmaceutically acceptable acid addition salt thereof, in which:
$R_1$ is hydrogen or lower alkyl and
$R_2$ is lower alkyl or
$R_1$ and $R_2$ together with the nitrogen atom to which they are attached form a pyrrolidine, piperidine, or perhydroazepine ring; and
$n$ is 2 or 3.

2. A compound according to claim 1 in which $R_1$ is hydrogen or lower alkyl and $R_2$ is lower alkyl.

3. A compound according to claim 2 in which $n$ is 2.

4. A compound according to claim 3 being the compound 3-(2-diethylaminoethoxy)-7-oxo-7H-benzo[b]phenaleno-[2,1-]furan.

5. A pharmaceutical composition having coronary vasodilator activity comprising a pharmaceutical carrier and in an effective amount to produce said activity a compound of claim 1.

6. A method of producing coronary vasodilation comprising administering internally to an animal in an effective amount to produce said activity a compound of claim 1.

* * * * *